United States Patent [19]

Broadbent et al.

[11] Patent Number: 4,804,839
[45] Date of Patent: Feb. 14, 1989

[54] HEATING SYSTEM FOR GC/MS INSTRUMENTS

[75] Inventors: Carolyn C. Broadbent, Los Altos; John C. Fjeldsted, Redwood City, both of Calif.

[73] Assignee: Hewlett-Packard Company, Palo Alto, Calif.

[21] Appl. No.: 70,458

[22] Filed: Jul. 7, 1987

[51] Int. Cl.[4] .............................. H01J 49/04
[52] U.S. Cl. .................... 250/288; 250/281; 250/282
[58] Field of Search .............. 250/281, 282, 288 A, 250/288; 219/301, 302

[56] References Cited

U.S. PATENT DOCUMENTS 4,298,795 11/1981 Takeuchi et al. ............ 250/288 A
4,484,061 11/1984 Zelinka et al. ............... 219/301

Primary Examiner—Carolyn E. Fields
Assistant Examiner—John A. Miller

[57] ABSTRACT

In a gas chromatograph/mass spectrometer (GC/MS) instrument, an improved heating system includes an interface between the gas chromatograph and mass spectrometer portions of the instrument, a radiator located within a vacuum chamber of the mass spectrometer, a thermal coupler attaching the interface to the radiator, and a heat source which directly heats the interface and indirectly heats the radiator via conduction through the thermal coupler. The heating system uses a single heating element located externally to the vacuum system of the mass spectrometer to produce a multiplicity of temperatures for the interface and various portions of the mass spectrometer.

9 Claims, 3 Drawing Sheets

HEATING SYSTEM FOR GC/MS INSTRUMENTS

BACKGROUND OF THE INVENTION

1. Field of the Invention

This invention relates generally to analytical instruments, and more particularly to instruments which include the combination of a gas chromatograph and a mass spectrometer.

2. Description of the Related Art

A gas chromatograph (GC) is an analytical instrument which can separate a gaseous mixture into its various constituent parts. A mass spectrometer (MS) is an analytical instrument which can analyze a gaseous sample to determine its molecular structure. When the output of a gas chromatograph is coupled to the input of a mass spectrometer, the combination instrument is known as a gas chromatograph/mass spectrometer (GC/MS).

Both gas chromatographs and mass spectrometers have been around for a relatively long period of time. However, combination GC/MS instruments are relatively recent innovations, and continuing research and development is directed towards improving the interface between the gas chromatograph and the mass spectrometer portions of GC/MS instruments.

A typical GC/MS interface includes a tubular transfer line having one end coupled to the output of the gas chromatograph and having its other end extending into a vacuum chamber of the mass spectrometer. An ion source of the mass spectrometer is used to ionize the effluent from the transfer line, and a quadrupole filter of the mass spectrometer is used to filter the ionized components of the gas according to mass. An ion detector within the vacuum chamber of the mass spectrometer detects ions filtered through the quadrupole filter. Finally, the recorded output signal of the detector is studied to determine the chemical structure of the gas sample.

A problem with prior art GC/MS interfaces is the complexity and cost of the associated heating systems. In a GC/MS instrument, the interface should be kept very hot to maintain the temperature of the gaseous sample flowing from gas chromatograph. Within the mass spectrometer, the ion source should be hot, the quadrupole should be moderately hot, and the ion detector should be at, or slightly above, ambient temperature.

In the past, this range of temperatures has been accomplished by providing separate heaters for the interface, ion source, and quadrupole. In consequence, prior art GC/MS instruments have a complex assemblage of heaters and associated controllers, each of which adds to the cost and complexity, and reduces the reliability, of the instrument. These problems were compounded by the fact that two of the three heaters (i.e. the heaters for the ion source and the quadrupole) were internal to the vacuum system of the mass spectrometer, and were therefore difficult to access for adjustment, repair, or replacement.

SUMMARY OF THE INVENTION

An object of this invention is to provide a reliable, economical heating system for GC/MS instruments.

Briefly, the invention includes a transfer line, a radiator located within a vacuum chamber of a mass spectrometer, a thermal coupler coupling the radiator to the transfer line, and a heat source which directly heats the transfer line and which indirectly heats the radiator via thermal conduction from the transfer line through the thermal coupler. The thermal coupler is attached near one end of the radiator, such that a temperature gradient is created along the length of the radiator ranging from hot to cool. To accentuate this thermal gradient, the radiator can be provided with a thermal divider. A flexible, thermally resistive coupling is provided between the transfer line and the vacuum chamber of the mass spectrometer.

The heat source, which is clamped to the transfer line, provides the high temperatures required for heating the gas sample released by the gas chromatograph. A portion of the heat from the transfer line is conducted by the thermal coupler to the radiator to provide heating for the ion source and the quadrupole. By positioning the ion source of the mass spectrometer near the thermal coupler, and by positioning the quadrupole on the other side of the thermal divider, proper temperatures for the ion source and quadrupole can be maintained.

An advantage of this invention is that a single heater, provided externally to the vacuum system of a mass spectrometer, can provide a range of temperatures to various portions of a GC/MS instrument.

These and other objects and advantages of the present invention will become apparent to those skilled in the art after reading the following descriptions and studying the various figures of the drawing.

DETAILED DESCRIPTION OF THE PREFERRED EMBODIMENTS

Figure 1:
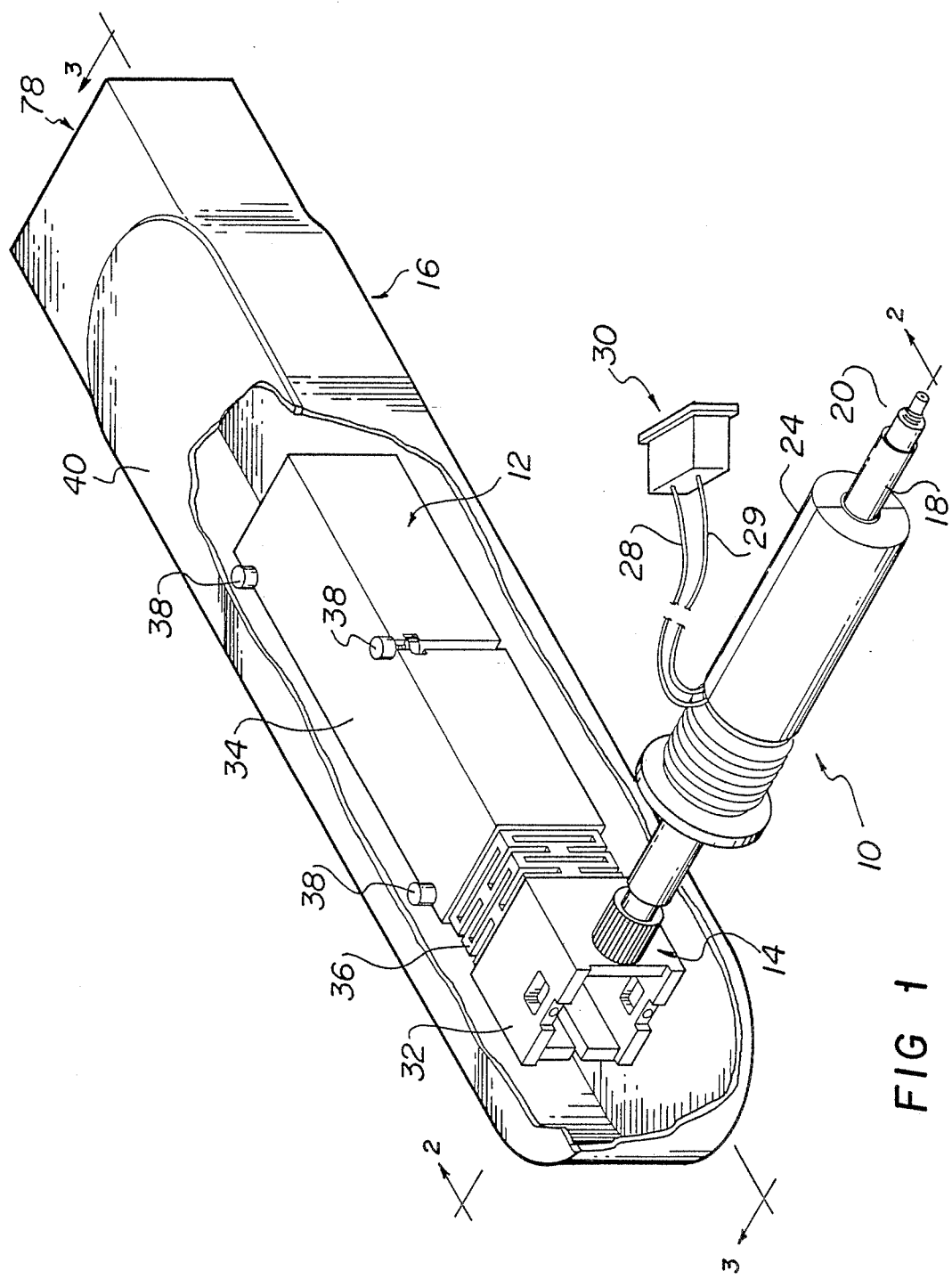
FIG. 1 is a partially broken, perspective view of a vacuum chamber of a GC/MS instrument and of the heating system of the present invention.

With reference to FIG. 1, an improved heating system for GC/MS instruments includes an interface assembly 10, a radiator 12, and a thermal coupler 14 attaching the interface assembly 10 to the radiator 12. A vacuum chamber 16 of a mass spectrometer fully encloses the radiator 12.

Figure 2:
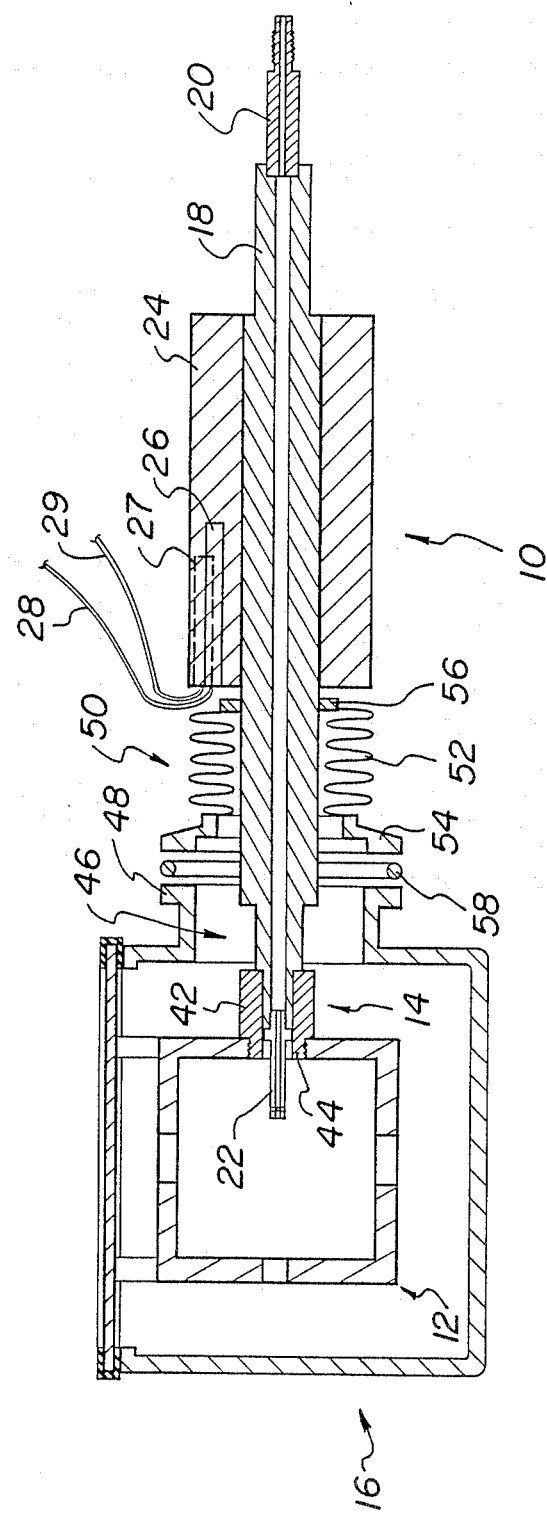
FIG. 2 is a cross-sectional view taken along line 2—2 of FIG. 1.

With additional reference to FIG. 2, the interface assembly 10 includes an elongated, tubular transfer line 18 having a transfer inlet 20 attached to one of its ends, and a transfer tip 22 attached to its other end. The transfer line 18, which is preferably made from copper, is surrounded by a jacket 24 which can be heated by a heating element 26. The temperature of the jacket 24 can be monitored by a thermal sensor 27 and controlled by a feedback circuit, the design of which is well known to those skilled in the art. The heating element 26 and sensor 27 are connected to power and control circuitry (not shown) by wires 28 and 29, respectively, and a connector 30.

Figure 3:
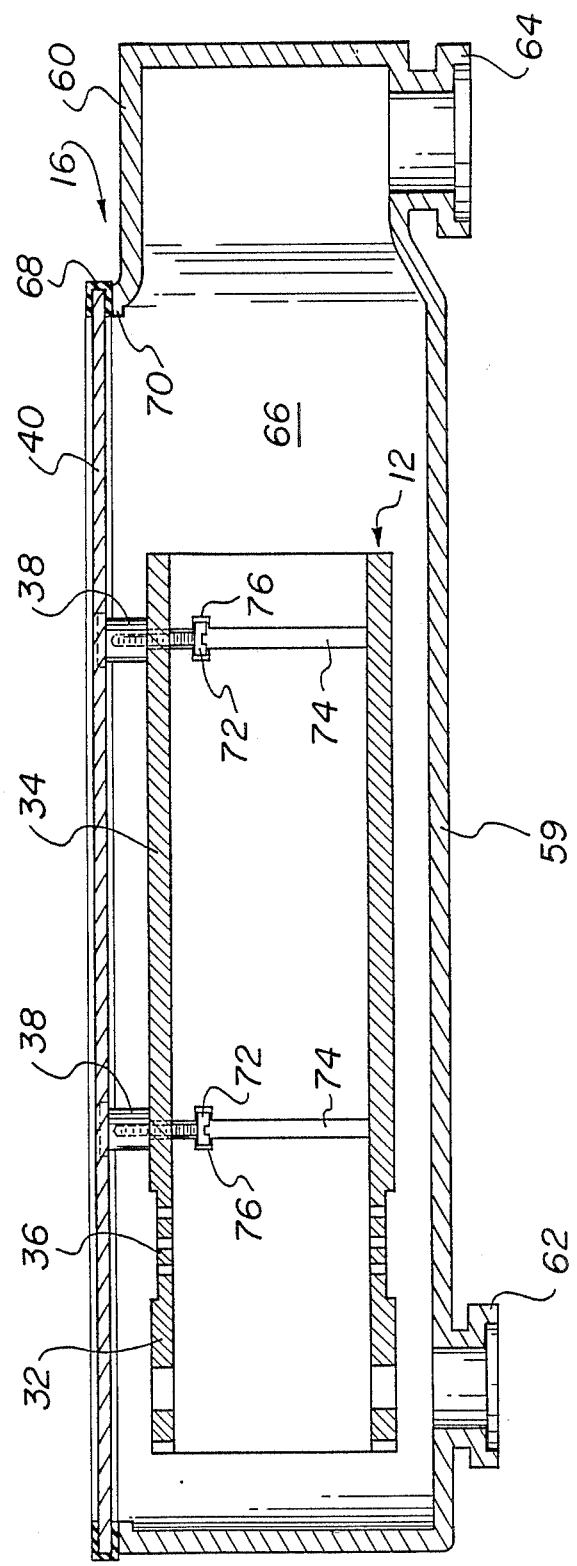
FIG. 3 is a cross-sectional view taken along line 3—3 of FIG. 1.
Figure 3:
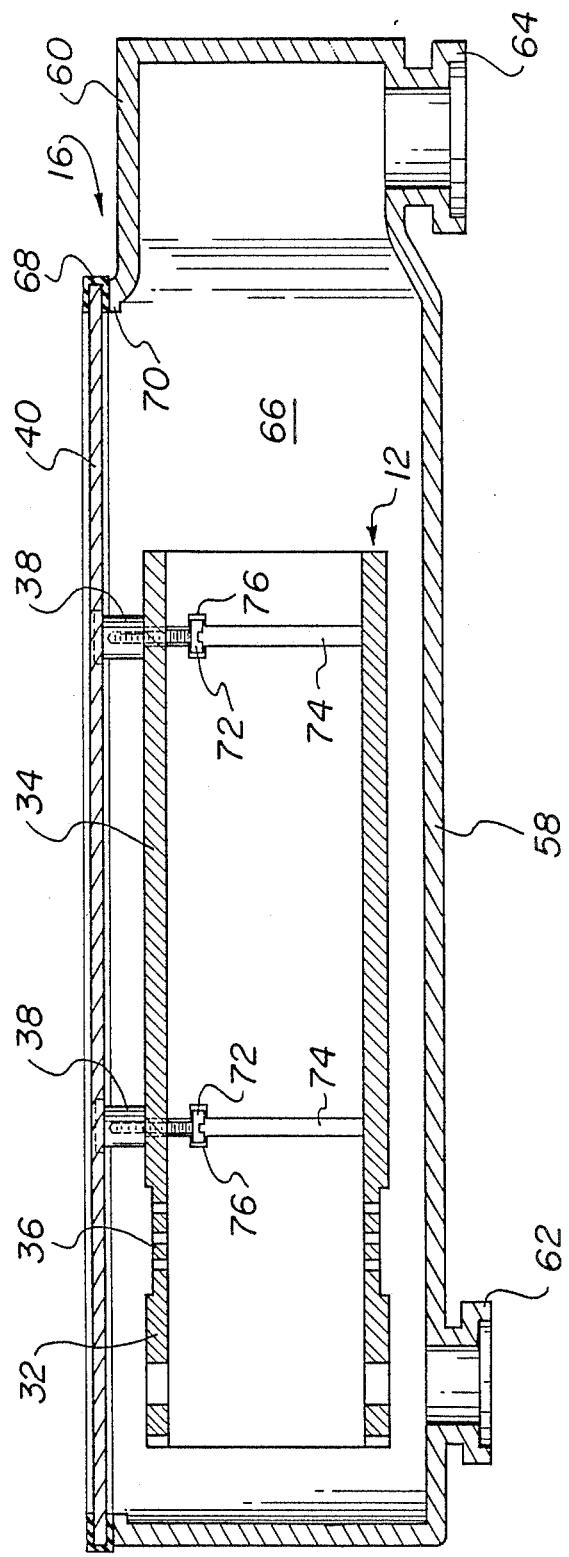

With reference to FIGS. 1 and 3, the radiator 12 is an elongated conduit having a substantially square cross-section, and includes an ion source section 32, a quadrupole section 34, and a thermal divider section 36. As will be discussed in greater detail subsequently, the radiator 12 is suspended within the vacuum chamber 16 by thin-wall stand-offs or spacers 38, which are attached to a base plate 40 of the vacuum chamber 16.

Referring now to FIGS. 1 and 2, the thermal coupler 14 includes a body portion 42 which engages the outlet end of transfer line 18, and a threaded portion 44 which engages a threaded bore provided in the ion source section 32 of radiator 12. The thermal coupler 14 should be made from a material having a high thermal conductivity, such as brass, so that it can efficiently conduct heat from the transfer line 18 to the radiator 12.

Still referring to FIG. 2, the vacuum chamber 16 is provided with an opening 46 having a flanged collar 48. A vacuum-tight, thermally-resistive coupling 50 is used to couple the transfer line 18 to the flanged collar 48 of the vacuum chamber 16. More specifically, coupling 50 includes a bellows portion 52, a flanged portion 54, and an annular portion 56 which attaches the bellow portions 52 to the transfer line 18. An O-ring 58 is disposed between flanged collar 48 of vacuum chamber 16 and the flanged portion 54 of the coupling 50 to provide a vacuum tight seal. A compressive clamp (not shown) firmly clamps flanged portions 48 and 54 together, sandwiching the O-ring 58 therebetween.

The bellow portion 52 of coupling 50 is designed to minimize heat transfer between the transfer line 18 and the vacuum chamber 16 while maintaining a vacuum-tight seal. The bellow portion 52, which is preferably made from a high thermal resistivity material such as stainless steel, is capable of resilient movement during heating, cooling, pump-down, and vent cycles, which ensures proper contact between the hot transfer line 18 and the thermal coupler 42.

Referring once again to FIG. 3, the vacuum chamber 16 includes a main body portion 59 and a narrowed, neck portion 60. The main body portion 59 is provided with a calibration inlet port 62, while neck portion 60 is provided with a vacuum port 64 which is coupled to a vacuum system (not shown) to maintain the internal volume 66 of vacuum chamber 16 at a sufficiently low pressure.

As mentioned previously, the radiator 12 is attached to the base plate 40 of the vacuum chamber 16 by thin-wall stand-offs or spacers 38. The base plate 40 is provided with a circumferential seal 68 which engages a surface 70 of the vacuum chamber 16. The base plate 40 is set against the sealing surface 70 with compressive clamps (not shown) to maintain a vacuum-tight seal.

The spacers 38 are preferably permanently attached to the inner surface of base plate 40 by any suitable process, such as welding. Each of the spacers 38 is provided with a threaded, axial bore receptive to the shank of a machine bolt 72. Appropriate grooves 74 and slots 76 are provided in the sidewalls of radiator 12 to allow for the engagement and disengagement of the machine bolts 72 with the spacers 38.

In operation, the transfer inlet 20 is coupled to the output of a gas chromatograph (not shown). The connector 30 is connected to control and power circuitry of the gas chromatograph. The transfer line 18 is heated by the heating element 26 by conduction through jacket 24 to provide substantially uniform heat to the 25 gas flowing through the transfer line. Heat is conducted through the hot transfer line 18 to the ion source section 32 of radiator 12 via thermal coupler 14. Because the thermal coupler 14 is attached near one end of the radiator 12, a thermal gradient is set up along the length of the radiator. This thermal gradient is accentuated by the thermal divider 36. By properly designing the thermal divider 36, the temperature differential between the ion source section 32 and the quadrupole section 34 can be accurately controlled.

Thus, the GC/MS heating system of the present invention utilizes a single heating element 26 to provide the various temperatures required by the transfer line, ion source, and quadrupole. For example, the heating element 26 could cause the transfer line 18 to become very hot (approximately 250° C.), the ion source section 32 of radiator 12 to become hot (approximately 190° C.), the quadrupole section 34 to become moderately hot (approximately 160° C.), and the ion detector (not shown) to remain warm (approximately 60° C.). Furthermore, the heating system of the present invention does not require any heating elements within the vacuum chamber of the mass spectrometer, greatly facilitating the adjustment, repair, and replacement of the heating elements.

While this invention has been described with reference to several preferred embodiments, it is contemplated that various alterations and permutations of the invention will become apparent to those skilled in the art upon a reading of the preceding descriptions and a study of the drawing. It is therefore intended that the scope of the present invention be determined by the following appended claims.

What is claimed is:

1. In a GC/MS system comprising a gas chromatograph, a mass spectrometer, interface means coupling an output of said gas chromatograph to an input of said mass spectrometer, and heating means for heating said interface means and portions of said mass spectrometer; improved heating means comprising:
   radiator means disposed within said mass spectrometer;
   thermal coupling means coupling said interface means to said radiator means; and
   a heat source means for directly heating said interface means and for indirectly heating said radiator means via thermal conduction from said interface means to said radiator means through said thermal coupling means.

2. Improved heating means for a GC/MS system as recited in claim 1 wherein said interface means is substantially uniformly heated by said heat source means, and wherein said radiator means is coupled to said interface means such that said radiator means develops a temperature gradient as it is conductively heated through said thermal coupling means.

3. Improved heating means for a GC/MS system as recited in claim 2 wherein said radiator means is provided with a thermal divider which separates a higher temperature portion from a lower temperature portion.

4. Improved heating means for a GC/MS system as recited in claim 3 wherein said heat source includes a jacket which at least partially surrounds said interface means.

5. Improved heating means for a GC/MS system as recited in claim 1 wherein said mass spectrometer includes a vacuum chamber which encloses said radiator.

6. Improved heating means for a GC/MS system as recited in claim 5 further including thermally resistant coupling means for coupling said interface means to said vacuum chamber.

7. Improved heating means for a GC/MS system as recited in claim 6 wherein said thermally resistant coupling means serves as a flexible vacuum seal.

8. Improved heating means for a GC/MS system as recited in claim 5 further comprising suspension means for suspending said radiator means within said vacuum chamber.

9. Improved heating means for a GC/MS system as recited in claim 1 wherein said radiator means at least partially surrounds an ion source assembly and a quadrupole assembly of said mass spectrometer.

* * * * *

UNITED STATES PATENT AND TRADEMARK OFFICE
CERTIFICATE OF CORRECTION

PATENT NO. : 4,804,839

DATED : February 14, 1989

INVENTOR(S) : Carolyn C. Broadbent and JOhn C. Fjeldsted

It is certified that error appears in the above-identified patent and that said Letters Patent is hereby corrected as shown below:

Column 3, Line 61, "the 25 gas flowing", should read

--- the gas flowing ---.

Signed and Sealed this

Twenty-sixth Day of September, 1989

Attest:

DONALD J. QUIGG

*Attesting Officer*   Commissioner of Patents and Trademarks